United States Patent [19]

Bentall

[11] 4,429,698

[45] Feb. 7, 1984

[54] HIGH FREQUENCY ELECTROMAGNETIC THERAPY APPARATUS

[76] Inventor: Richard H. C. Bentall, P.O. Box 47, London, W11, England

[21] Appl. No.: 205,749

[22] Filed: Nov. 10, 1980

Related U.S. Application Data

[63] Continuation of Ser. No. 74,926, Sep. 13, 1979, abandoned.

[51] Int. Cl.³ .............................................. A61N 1/40
[52] U.S. Cl. .................................................. 128/422
[58] Field of Search ............... 128/422, 804, 1.3, 784, 128/802

[56] References Cited

U.S. PATENT DOCUMENTS

| | | | |
|---|---|---|---|
| 2,276,996 | 3/1942 | Milinowski | 128/422 |
| 2,583,853 | 1/1952 | Kazdin | 128/804 |
| 2,656,839 | 10/1953 | Howard | 128/422 |
| 2,882,904 | 4/1959 | Rasmussin | 128/804 |
| 4,028,518 | 6/1977 | Boudouris et al. | 128/804 |
| 4,197,851 | 4/1980 | Fellus | 128/422 |

Primary Examiner—William E. Kamm
Attorney, Agent, or Firm—Steele, Gould & Fried

[57] ABSTRACT

A high frequency electromagnetic therapy apparatus having one or more flexible induction elements (such as sheathed electrically conductive wire) embodied in a flexible material (such as silicone rubber) and connected into the tuned LC circuit of a high frequency oscillator circuit whereby the frequency of the electromagnetic field produced by the apparatus is determined at least in part by the capacitive coupling between the induction elements and the area of the body being treated.

5 Claims, 2 Drawing Figures

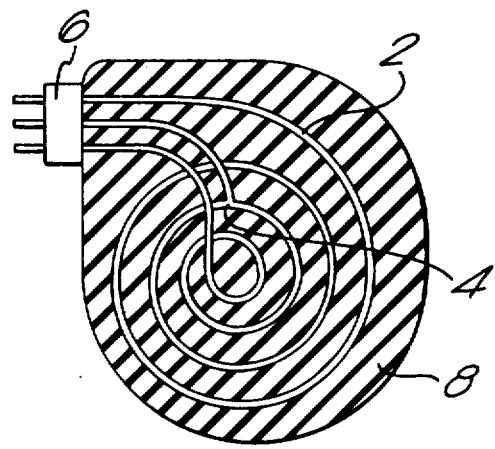
Fig. 1.
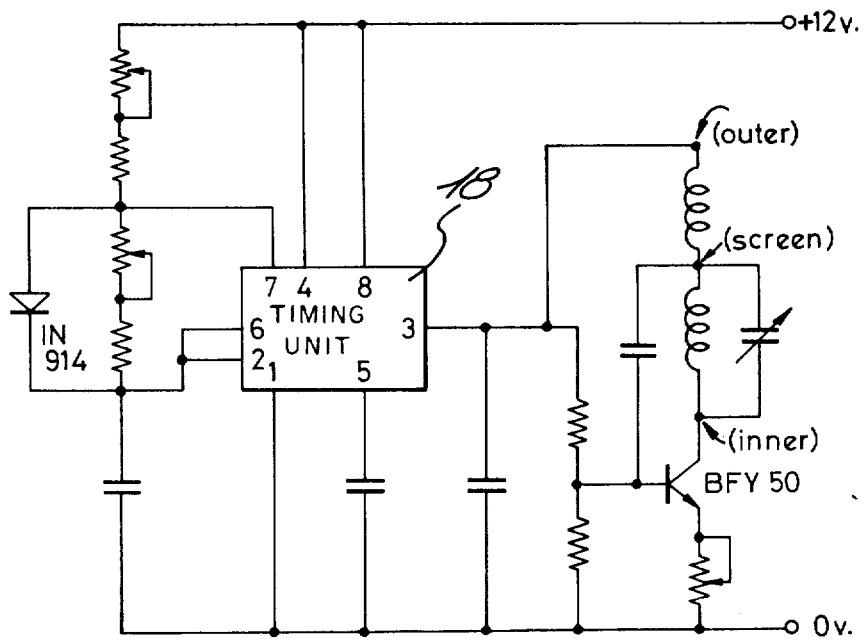

HIGH FREQUENCY ELECTROMAGNETIC THERAPY APPARATUS

CROSS-REFERENCE TO RELATED APPLICATION

This application is a continuation of co-pending application Ser. No. 074,926, filed Sept. 13, 1979, now abandoned.

This invention relates to high frequency electromagnetic therapy apparatus and to inductors for use with such apparatus.

For over forty years, high radio frequency electromagnetic radiation has been in regular use in the therapeutic treatment of a number of medical conditions. Many pathological processes have been successfully treated, by the direct application to the area under consideration, of an induced electromagnetic field in the VHF band. The Diapulse Corporation (New York, U.S.A.) produces a pulsed VHF electromagnetic field generator suitable for such medical use.

Present equipment is relatively high powered and is consequently large. The Diapulse Corporation equipment, for example, can produce a pulsed peak power of 900 watts and an average power output of 1.5 to 38 watts. The inductor which is placed adjacent the area to be treated is approximately the size of a domestic kettle and consequently the patient is somewhat restricted in movement during treating sessions.

It has recently been suggested in U.S. Pat. No. 4,197,851 that a smaller portable apparatus producing high-frequency, low-energy electromagnetic waves may be used instead of the present large, high-powered equipment. In this proposed apparatus a high frequency oscillator is connected via a matching circuit to a flexible antenna placed over the appropriate part of the patient. However, in such an arrangement the power adsorbed by the patient depends on matching of the fixed frequency of the oscillator with the capacitive coupling between the antenna and the patient. Since this capacitive coupling varies from patient to patient and from one part of the patient to another it can cause a loss of adsorbed power. Such power loss is critical in a low-powered apparatus where as much of the energy as possible must be transmitted to the patient.

According to the invention I provide a high frequency electromagnetic therapy apparatus comprising, a power supply, a flexible inductor having one or more induction elements embodied in a flexible material, so that it may be conformed to lie against an area of a body to be treated, and a high-frequency, low-energy signal generator circuit connectable between the power supply and the inductor to produce a high-frequency, low-energy electromagnetic field from the inductor, wherein the frequency of said field is determined by an LC tuned circuit and said inductor is part of the LC tuned circuit.

By providing the inductor as part of the LC tuned circuit changes in capacitive coupling between the inductor and the body to be treated merely cause a shift in the frequency of oscillation with no loss of adsorbed power.

By providing the inductor as a flexible body, it may be conveniently attached to the patient by means of surgical tape and will lie naturally against the area to be treated.

Normally the inductor will be generally planar, but for treatment of acutely curved areas of the body, it may be more convenient to form the inductor as a complementary curved surface.

The inductor elements may be wound, in a spiral. The number of turns provided, and any tapping points, will need to be exactly determined to provide the appropriate resonating frequency.

The inductor elements are generally electrically-conductive wire, for example multifilament wire, or other flexible conductive material. More than one inductor element may be employed if desired.

To form the treatment inductors, the inductor elements can be laid in the pattern required and then provided with a flexible cover, for example, of silicone rubber. Various patterns may be provided for different areas of the body and if a generally-planar inductor is required then the product will generally be a sheet-like body of resilient material having the inductor elements embedded therein and having connector leads extending from one edge, for connection to the high frequency electromagnetic radiation generator. The latter is generally a miniaturised VHF pulse generator. The power generated by such apparatus (functioning from small batteries) is in the milliwatt region.

Preferred features of the invention will now be described with reference to the accompanying drawings, wherein:

FIG. 1 is a schematic plan view in cross-section of a treatment inductor for use in the invention, and FIG. 2 is a circuit diagram of a miniature VHF pulse generator and a treatment inductor according to the invention.

FIG. 1 illustrates a treatment inductor which is to form part of a tuned circuit with a VHF pulse generator. The inductor comprises a spirally-wound, sheathed multifilament electrically-conductive wire 2 having a centre-tapping 4. This provides a three-pin connection 6 from the two ends and the centre of the wire. The wire is embedded in silicone rubber 8 and the whole inductor is of generally-planar appearance.

FIG. 2 is a circuit diagram of a self-oscillating VHF pulse generator with a three-pin treatment inductor. The latter consists of a spirally-wound coaxial cable, similar to the inductor shown in FIG. 1, but with the centre-tapping of the cable being taken to the screen and the outer and inner connections being made to the central conductor of the cable. The inductor winding connections are shown to the right of FIG. 2.

The pulse generator includes a timing-unit 18 (Type 555 available from Radio Spares, London, U.K.) feeding a power amplifier output stage which itself provides outputs for connection to the three pins of the treatment inductor already mentioned. The circuit illustrated provides 12 volt output pulses from pin 3 of the oscillator, 100 $\mu$sec. in width and at intervals of 1 msec. The inductor coil was formed of coaxial cable with cable lengths: outer connection to screen connection 79 cm, screen connection to inner connection 57 cm. The generally circular electrode produced was approximately 10 cm. in diameter and produced a power output in the milliwatt range.

The frequency of the field produced from the treatment inductor is determined in part by the inductance L of the inductor windings and by the capacitance C across the windings. Capacitive coupling with the body being treated changes the effective capacitance and causes a slight shift in the frequency.

I claim:

1. A high frequency electromagnetic therapy apparatus, comprising:
   a power supply;
   a flexible inductor of generally circular configuration forming an antenna which is positionable on an area of a body to be treated; and,
   a high-frequency, low-energy signal oscillating circuit for generating a high-frequency, low-energy electromagnetic field radiated from the inductor-antenna, at a power level in the milliwatt range, into the area of the body to be treated at an adsorbed power level in the same power range, which promotes healing of body tissue, but which is too small to significantly heat the body tissue, the frequency of said radiated field being controlled by an inductive-capacitive tuned circuit, said inductor-antenna forming all of the inductive portion of the tuned circuit, the power level of the adsorbed field being independent of differences in capacitive coupling between the inductor-antenna and different parts of the body to be treated, the differences in coupling resulting in negligible power loss of the adsorbed field relative to the radiated field and inconsequential frequency shift, whereby an impedance matching circuit for the antenna is unnecessary.

2. An apparatus according to claim 1, wherein the inductor-antenna is a spiral of at least one turn.

3. An apparatus according to claims 1 or 2, wherein the flexible inductor-antenna comprises a plurality of inductor elements defined between tapping points on a spiral wound electrical conductor.

4. An apparatus according to claim 1, further comprising a fixed frequency pulse generator for driving the oscillating circuit.

5. An improved high frequency electromagnetic therapy apparatus, having a power supply, having a flexible antenna of generally circular configuration which is positionable on an area of a body to be treated and having a high-frequency, low-energy oscillating generator circuit for radiating a high-frequency, low-energy electromagnetic field from the antenna, at a power level not greater than a level in the range of milliwatts, the improvement comprising:
   an inductive-capacitive tuned circuit for controlling the frequency of the field; and,
   the flexible antenna forming all of the inductive portion of the tuned circuit, the power level of the adsorbed field being in the same range as the radiated power, the adsorbed power level being sufficient to promote healing of body tissue, but being too small to significantly heat the body tissue, and the power level being independent of the differences in capacitive coupling between the inductor-antenna and different parts of the body to be treated, the differences in coupling resulting in negligible power loss of the adsorbed field relative to the radiated field and inconsequential frequency shift, whereby an impedance matching circuit for the antenna is unnecessary.

* * * * *